(12) United States Patent
Giovannone

(10) Patent No.: US 6,755,351 B2
(45) Date of Patent: Jun. 29, 2004

(54) SUSPENDED CONTAINER FOR ESSENCES WITH MEANS FOR THEIR ABSORPTION AND DIFFUSION OF THEIR PERFUME TO THE SURROUNDING AMBIENT

(76) Inventor: Alberto Giovannone, Via Ugo Pepe 10, 20020 Busto Garolfo (IT)

( * ) Notice: Subject to any disclaimer, the term of this patent is extended or adjusted under 35 U.S.C. 154(b) by 0 days.

(21) Appl. No.: 10/258,434
(22) PCT Filed: Apr. 17, 2001
(86) PCT No.: PCT/IB01/00634
§ 371 (c)(1),
(2), (4) Date: Oct. 24, 2002
(87) PCT Pub. No.: WO01/82982
PCT Pub. Date: Nov. 8, 2001

(65) Prior Publication Data
US 2003/0071137 A1 Apr. 17, 2003

(30) Foreign Application Priority Data
Apr. 28, 2000 (IT) .................... CO2000U0005

(51) Int. Cl.$^7$ .......................... A24F 25/00; A61L 9/04
(52) U.S. Cl. ............................... 239/44; 239/34
(58) Field of Search ................. 239/44, 34, 57, 239/47, 48, 145; 43/1

(56) References Cited
U.S. PATENT DOCUMENTS

| 2,572,329 A | * 10/1951 | Foster ..................... 239/45 |
| 3,724,756 A | * 4/1973 | Maltenfort ................ 239/47 |
| 4,742,960 A | * 5/1988 | Bustillo et al. ........... 239/47 |
| 5,261,570 A | * 11/1993 | Hippely et al. .......... 222/212 |
| 5,437,410 A | 8/1995 | Babasade |
| 5,622,314 A | 4/1997 | Eason |
| 5,947,379 A | * 9/1999 | Freeman ................... 239/52 |

FOREIGN PATENT DOCUMENTS

| FR | 2 720 608 A | 12/1995 |
| WO | WO 00 67807 A | 11/2000 |

OTHER PUBLICATIONS

Patent Abstracts of Japan, vol. 1998, No. 14, Dec. 31,1998.
Patent Abstracts of Japan vol. 1998, No. 13, Nov. 30, 1998.
Patent Abstracts of Japan, vol. 1995, No. 02, Mar. 31, 1995.

* cited by examiner

Primary Examiner—Michael Mar
Assistant Examiner—Darren Gorman
(74) Attorney, Agent, or Firm—Young & Thompson

(57) ABSTRACT

Herein is described a container (4) holding in its cavity (2) perfumed essences (3), provided with a stopper (4) and hanging means for the container (1) when hooked to a fixed support, where said means are made up of one or more threadlike elements (5), which pass through the stopper (4) in such a way that a section (5d) can come into contact with the perfumed essences (3) and are produced in a material suitable to absorb them and permit their propagation through capillary action along their length.

8 Claims, 3 Drawing Sheets

SUSPENDED CONTAINER FOR ESSENCES WITH MEANS FOR THEIR ABSORPTION AND DIFFUSION OF THEIR PERFUME TO THE SURROUNDING AMBIENT

BACKGROUND OF THE INVENTION

This invention refers to the technological field of containers for perfumed essences to be used in closed surroundings (bathrooms, cars, etc.) to deodorise and perfume by means of gradual evaporation.

More in detail, the invention concerns the type of these containers, provided with hanging means, connected to the stopper, which makes it possible to hang them from a fixed support (hook, rear mirror, etc.) in the surroundings to be perfumed.

The same applicant has described this type of container in previous applications, for example PCT/IB00/00175.

According to the present state-of-art, the containers for perfumed essences are hung by means of various systems, for example by means of a cord tied around the neck just below the stopper, which keeps them fixed.

When the latter is made of porous material, such as wood or similar, it absorbs the essence to give off the perfume but, being in contact with said cords, they become damp causing a questionable aesthetic result as they are soaked with the liquid, impairing with time the necessary characteristics of duration and mechanical resistance.

Furthermore, these cords are noticeably expensive compared to the selling price of the container.

SUMMARY OF THE INVENTION

The inventor of this invention has conceived a new type of container where the hanging means are also meant for the emanation of the perfume, being made of a threadlike element in a material suitable to absorb the perfumed essences, transferring part of them with a capillary action to the outside of the container without undergoing any physical-chemical deterioration and without moistening the external surfaces with the essence.

In fact, the subject of this invention consists in a container holding perfumed essences.

Hereunder is a more detailed description of some examples of the container according to the invention, but this description is not intended as limiting or binding regarding other possible embodiments obtainable on the basis of the teachings of the above-mentioned embodiment.

BRIEF DESCRIPTION OF THE DRAWINGS

During this description, reference will also be made to the enclosed drawings, which represent.

DETAILED DESCRIPTION OF THE PREFERRED EMBODIMENTS

Figure 1:
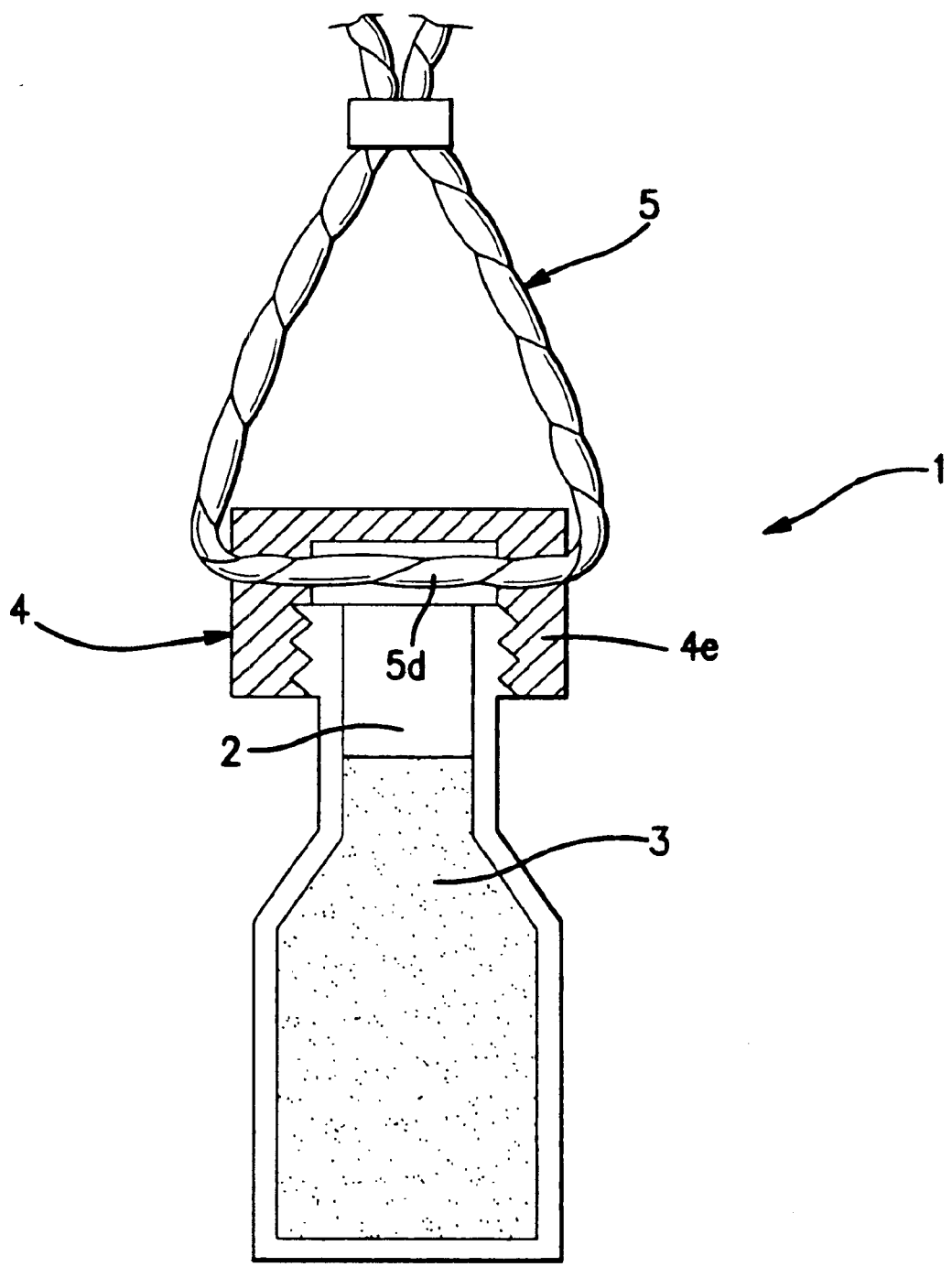
in FIG. 1, the longitudinal section of an embodiment of the container subject of this invention, in which a plaited cord transversally crosses the stopper.

In FIG. 1 it can be seen how, in the embodiment shown, the hanging means of a container 1 according to the invention are made up of a plaited cord 5 which transversally crosses the stopper 4, in such a way as to leave a section 5d open between the lateral walls 4e of the latter, in an area above the cavity 2 of the container 1. Turning the container upside-down, this section 5d is soaked with the perfumed essence 3 inside which is then transferred in part to the outside, due to known capillary action, where it evaporates gradually without noticeably dampening the external surface of the cord 5.

Figure 2:
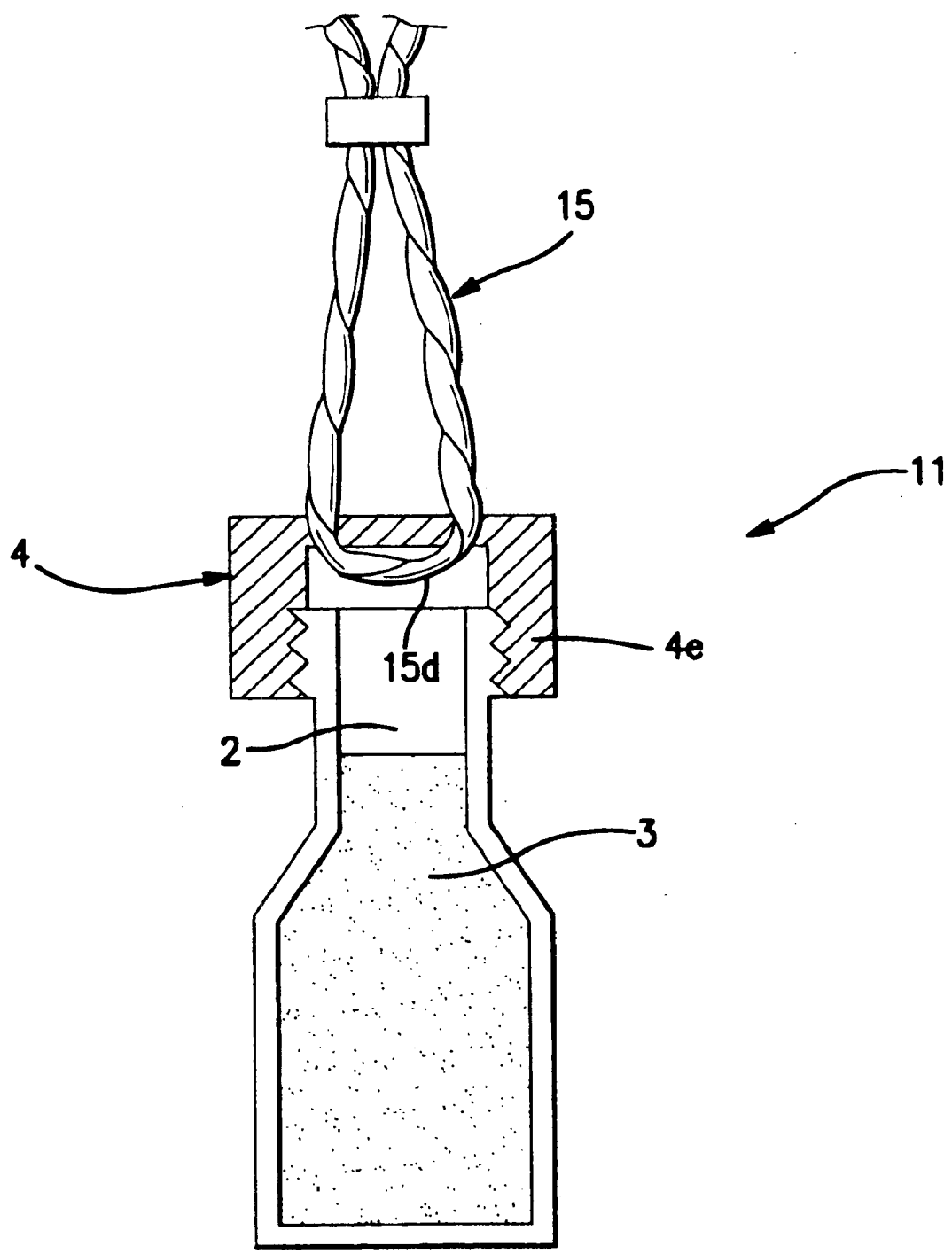
in FIG. 2, the longitudinal section of another embodiment in which a plaited cord enters and exits the stopper by means of two holes in its upper surface.

Another possible embodiment of a container 11 according to the invention is shown in FIG. 2: in this case, a plaited cord 15 enters and exits the stopper 4 through two holes 6, 7 in the upper surface, leaving a section open 15d between its lateral walls 4e in a similar position to the case considered previously.

Figure 3:
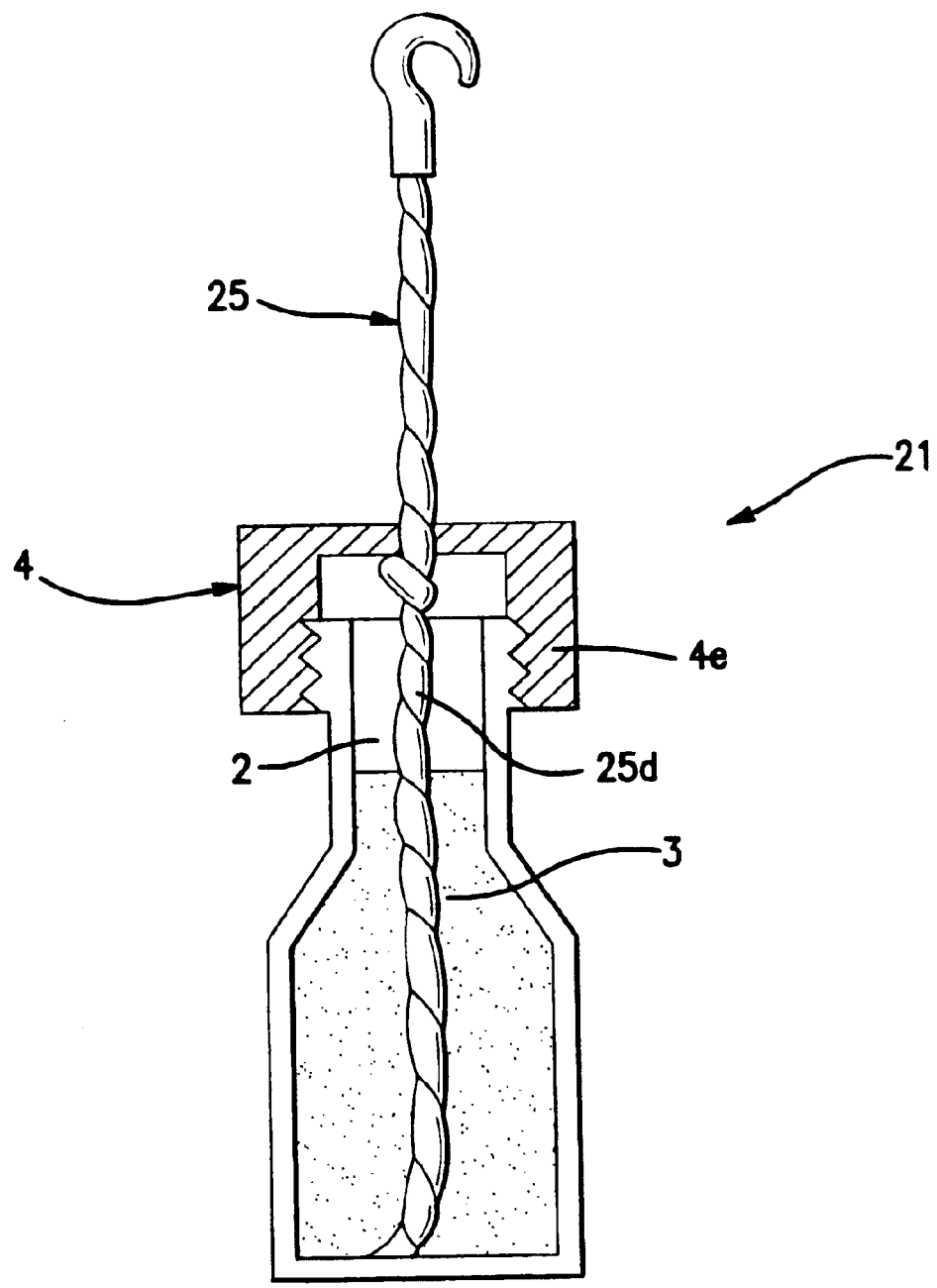
in FIG. 3, the longitudinal section of another embodiment in which a plaited cord penetrates into the cavity of the container through a single hole in the upper surface of the stopper.

Also in this case, by turning the container 11 upside-down, the effect described above for the previous embodiment is obtained. Finally, in the embodiment shown in FIG. 3, the hanging means 5 according to the invention consist in a plaited cord 25 which goes through a hole 8 in the upper surface of the stopper 4, having an open section 25d between its lateral walls 4e and in the direction of the cavity 2 of the container 21.

The cord 25 is fixed even by means of a simple knot 9 in such a way that it can be slipped off the stopper 4. Depending on whether or not the said open section 25d penetrates into the cavity 2 of the container 21, similar operation to that already described for the two previous cases can be obtained, or the cord 25 can be used as a "wick" diffuser. Evidently, to this end, it must penetrate into the cavity 2 until it touches the bottom of the container 21, as shown in the figure.

In all three cases described above, the cord 5, 15, 25, which constitutes the hanging means for the container 1, 11, 21, also acts as diffuser, and the stopper 4 can be produced in all the non-absorbent materials known to the skilled-in-the-art. Nothing prevents the production of this stopper in porous absorbent materials, such as wood or similar, so as to increase the amount of evaporation and, therefore, the perfuming effect wherever necessary. Concerning the means 5, 15, 25 for hanging the container, they can be produced in cord in natural or synthetic fibre, or in material, or plaited as shown in the figures. Other types of suitable materials can be used without problem.

What is claimed is:

1. A container comprising:

a cavity containing perfumed essence;

a stopper enclosing said perfumed essence within said cavity and defining a space between said stopper and said perfumed essence; and a cord extending into said stopper, into said space and extending through said stopper, outside said space without contacting said perfumed essence, wherein said cord is one of natural and synthetic materials suitable to absorb said perfumed essence and diffuse said perfumed essence through capillary action.

2. The container as claimed in claim 1, wherein said stopper comprises first and second holes said cord extending into said space through said first hole and out of said space through said second hole.

3. The container as claimed in claim 2, wherein the first and second holes are on opposing sides of said stopper.

4. The container as claimed in claim 2, wherein the first and second holes are on a same surface of said stopper.

5. A container comprising:

a cavity containing perfumed essence;

a stopper enclosing said perfumed essence within said cavity and defining a space between said stopper and said perfumed essence; and a cord extending into said stopper, into said space and extending through said stopper, outside said space without contacting said perfumed essence, wherein said stopper is porous.

6. A container having an opening, said container comprising:

a cavity containing perfumed essence;

a threaded neck adjacent said opening;

a stopper engageable with said threaded neck and closing said opening, said stopper comprising a top to contain said perfumed essence and a threaded circumferential sidewall depending from said top, a volume bounded by said threaded sidewall being free of perfumed essence while the container is in a first position; and a cord extending through said stopper only into said volume, said container being movable from said first position to an inverted second position so that said perfumed essence contacts the cord in the second position such that the perfumed essence is evaporatable through the cord to atmosphere when the cord is returned to said first position.

7. The container as claimed in claim 6, wherein said cord is through said sidewall.

8. The container as claimed in claim 6, wherein said cord is through said top.

* * * * *